United States Patent [19]

Hooks, Jr. et al.

[11] 3,954,781
[45] May 4, 1976

[54] PROCESS FOR PREPARING BIS(2-PYRIDYL-1-OXIDE) DISULFIDE

[75] Inventors: Haywood Hooks, Jr., West Haven; James J. Pitts, Hamden, both of Conn.

[73] Assignee: Olin Corporation, New Haven, Conn.

[22] Filed: Apr. 22, 1975

[21] Appl. No.: 570,935

[52] U.S. Cl. ............ 260/294.8 J; 260/294.8 G
[51] Int. Cl.$^2$ ........................... C07D 213/34
[58] Field of Search ........... 260/294.8 J, 294.8 G; 218/221

[56] References Cited
UNITED STATES PATENTS

| | | | |
|---|---|---|---|
| 2,742,476 | 4/1956 | Bernstein et al. | 260/294.8 J |
| 3,700,676 | 10/1972 | Damico | 260/294.8 G |

OTHER PUBLICATIONS

Klingsberg, Pyridine And Its Derivatives, Part 4, pp. 363, Interscience Publishers, (1964).
Klingsberg et al., J. Am. Chem. Soc., Vol. 71, pp. 2373–2374, July 1949.
King et al., J. Chem. Soc., London, pp. 873–877, (1939).

*Primary Examiner*—Alan L. Rotman
*Attorney, Agent, or Firm*—Robert L. Andersen

[57] ABSTRACT

An improved integrated route to bis(2-pyridyl-1-oxide) disulfide is provided wherein a solution of 2-mercaptopyridine-1-oxide formed by oxidizing 2-chloropyridine with peracetic acid to form a reaction mixture of 2-chloropyridine-1-oxide which is then mercaptized, is reacted with in situ generated hypochlorous acid at a pH in the range of 4-8, the hypochlorous acid being generated by chlorinating the solution of 2-mercaptopyridine-1-oxide in the presence of a base selected from the group consisting of an alkali metal hydroxide, carbonate, bicarbonate or combinations thereof.

11 Claims, No Drawings

PROCESS FOR PREPARING BIS(2-PYRIDYL-1-OXIDE) DISULFIDE

BACKGROUND OF THE INVENTION

This invention relates to an improved process for preparation of bis-(2-pyridyl-1-oxide) disulfide by oxidation of a solution of 2-mercaptopyridine-1-oxide, prepared via the peracetic acid route, with hypochlorous acid under controlled pH conditions.

U.S. Pat. No. 2,742,476 discloses generally the preparation of bis-(2-pyridyl-1-oxide) disulfide, also known as 2,2′-dithiodipyridine-1-1′-dioxide, hereinafter sometimes referred to as "the disulfide", by the general process in which a 2-mercaptopyridine-1-oxide is oxidized with an oxidizing agent of the peroxide type. U.S. Pat. No. 3,759,932 discloses the preparation of bis(2-pyridyl) disulfide by an integrated in situ route wherein the mercaptopyridine intermediate is oxidized without isolation with hydrogen peroxide. In our prior co-pending application Ser. No. 466,328, now U.S. Pat. No. 3,892,760 it was disclosed that in an integrated in situ process where permaleic acid was utilized in the initial oxidation step to convert 2-chloropyridine to 2-chloropyridine oxide followed by a subsequent peroxide oxidation of an intermediate mercaptopyridine-1-oxide, a preliminary pH adjustment to pH 4–6 was required in order to avoid certain precipitates caused by the initial use of permaleic acid.

It is also known that chlorine may be utilized in an integrated in situ process to oxidize 2-mercaptopyridine-1-oxide and its salts to the disulfide. The use of chlorine instead of peroxide is extremely desirable due to the inherent dangers implied in the handling of peroxides, due to the capital outlays for special equipment required to handle the latter safely and due to the cost differential between peroxide and chlorine. However, chlorine has been found to be unsuitable for the final oxidation in an integrated process utilizing permaleic acid in the initial oxidation of 2-chloropyridine to 2-chloropyridine-1-oxide. In such a system, the chlorine substitutes across the double bond of the permaleic acid and produces insoluble chlorinated by-products which preceipitate with the disulfide, complicate recovery and reduce yields.

On the other hand where peracetic acid is utilized as the initial oxidant to convert 2-chloropyridine to 2-chloropyridine-1-oxide in an integrated in situ system, chlorine has been utilized as the oxidant to convert the intermediate 2-mercaptopyridine-1-oxide to the disulfide. In prior processes utilizing chlorine, large excesses of chlorine were utilized in order to obtain yields which were barely adequate. Thus, chlorine was found to be a less satisfactory oxidant than peroxide.

We have now found that chlorine efficiency and yields may advantageously increase by chlorinating a solution of 2-mercaptopyridine-1-oxide under pH conditions conducive to the in situ formation of hypochlorous acid, namely at or to a pH in the range of 4 to 8 in the presence of a base selected from the group consisting of an alkali metal hydroxide, carbonate, or bicarbonate.

DESCRIPTION OF THE INVENTION

The process of the present invention is carried out in connection with an integrated in situ process for converting 2-chloropyridine to a solution of 2-mercaptopyridine-1-oxide without isolation or purification of intermediates. The overall scheme of the reaction system is shown by the following:

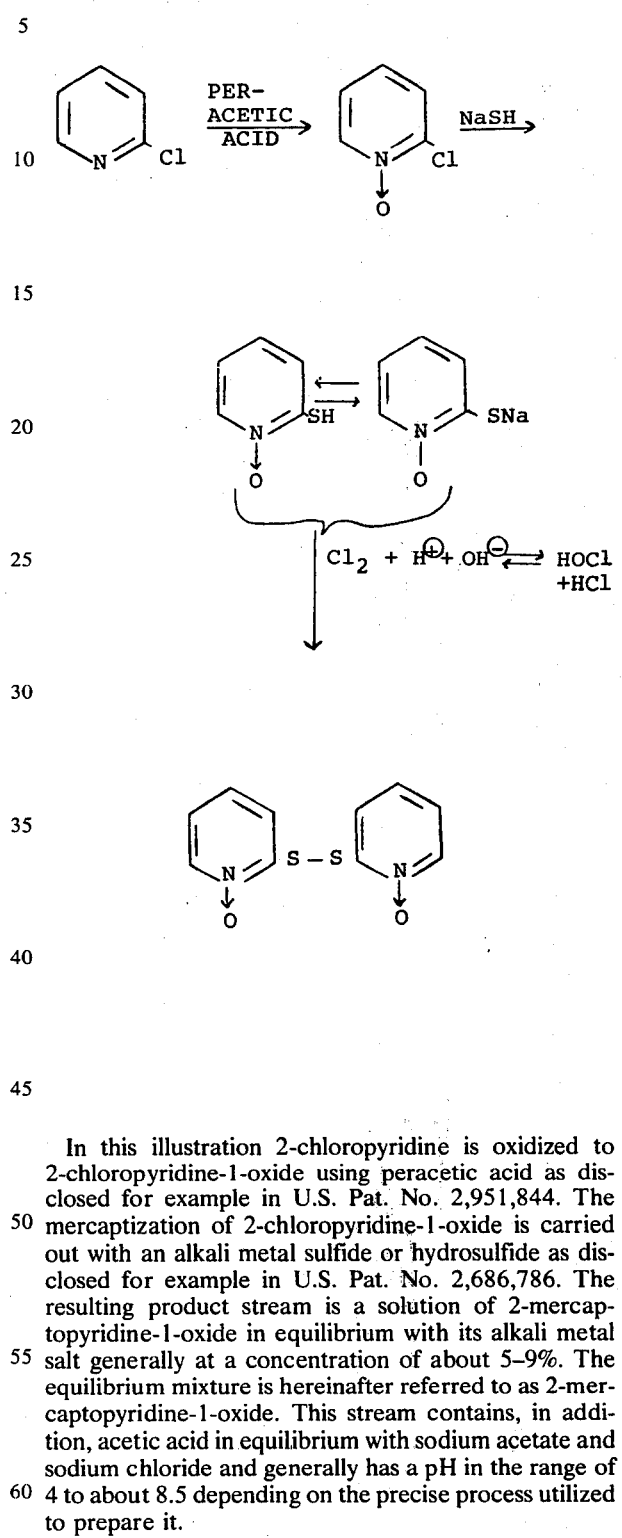

In this illustration 2-chloropyridine is oxidized to 2-chloropyridine-1-oxide using peracetic acid as disclosed for example in U.S. Pat. No. 2,951,844. The mercaptization of 2-chloropyridine-1-oxide is carried out with an alkali metal sulfide or hydrosulfide as disclosed for example in U.S. Pat. No. 2,686,786. The resulting product stream is a solution of 2-mercaptopyridine-1-oxide in equilibrium with its alkali metal salt generally at a concentration of about 5–9%. The equilibrium mixture is hereinafter referred to as 2-mercaptopyridine-1-oxide. This stream contains, in addition, acetic acid in equilibrium with sodium acetate and sodium chloride and generally has a pH in the range of 4 to about 8.5 depending on the precise process utilized to prepare it.

Prior to the present invention, this stream would have been chlorinated directly, without any pH adjustment or control, and in particular without utilizing additional base to effect pH control. As chlorination was started, pH of the solution dropped rapidly below 4 and was continued at a pH below 4 where chlorine was quite inefficient in oxidizing or reacting with the 2-mercaptopyridine-1-oxide to form the disulfide. As indicated above, the result was that much chlorine was wasted and yields were low. The only solution to inefficient use of chlorine and low yields prior to the present invention seemed to be in slowing down chlorination and increasing reaction time. This, however, was a commercially unacceptable solution in that overall productivity was not improved.

In accordance with the present invention yields are improved to about 75 to 85% with a stoichiometric amount or slight excess of chlorine without extending reaction times. It has been found that the key to this improved result lies in conducting the reaction between chlorine and a suitable base under conditions conducive to the in situ formation of hypochlorous acid which then selectively reacts with 2-mercaptopyridine-1-oxide to form the disulfide.

At least two embodiments of the invention are contemplated. In the first, the solution of 2-mercaptopyridine-1-oxide produced as described above, namely by oxidizing 2-chloropyridine to the 1-oxide with peracetic acid and then mercaptizing, is basified as required to a pH in the range of 8–12, preferably 10–12, with an alkali metal hydroxide, bicarbonate, or carbonate. Preferably an aqueous solution thereof is utilized with the preferred alkali metal being sodium. Thus, sodium hydroxide, sodium bicarbonate, or sodium bicarbonate, or a mixture thereof is preferred.

The basified solution is then chlorinated in any known manner, but preferably by bubbling gaseous chlorine through the solution. As chlorination proceeds initially most, if not all chlorine supplied is taken up in solution, presumably as hypochlorite ion. The pH of the reaction mixture drops during chlorination and as the pH drops oxidation becomes apparent by the rapid formation of the precipitating disulfide. If sodium hydroxide was used for the pH adjustment, this becomes apparent at a pH below about 7, preferably below about 6.8. With sodium bicarbonate it becomes apparent when the pH decreases to below about 8, advantageously below about 7.6, preferably below about 7.4.

Chlorination, however, is continued beyond this point until a stoichiometric or slight molar excess of chlorine has been added, more particularly until at least 1.0, suitably 1.0–2.0, preferably 1.0–1.5, moles of chlorine have been added per mole of 2-mercaptopyridine-1-oxide.

During the terminal stages of chlorination, the pH of the reaction mixture may drop to a pH below 4 if not controlled, and this will cause a rapid decrease in yields of the disulfide and in oxidative efficiency of the chlorine utilized.

It is thus apparent that the reaction in which the 2-mercaptopyridine-1-oxide is oxidized to bis-(2-pyridyl-1-oxide) disulfide occurs when the pH of the reaction mixture is in the range of 4–8, advantageously 4–7.6, preferably 5–7.6 that no significant reaction occurs above a pH of about 8, and that if the pH is allowed to fall below about 4 yields and chlorine efficiency are markedly reduced.

If additional pH control is required during the terminal stages of chlorination in order to maintain the pH within the desired range, a strong highly dissociated rapidly reacting base such as sodium hydroxide is added as required.

In this embodiment, the initial adjustment to a pH in the range of 8–12, preferably 10 to 12, does not adversely affect yields or chlorine efficiency and may, in fact, benefically affect both. Nevertheless the pH above about 12 should be avoided to prevent caustic attack on the 2-mercaptopyridine-1-oxide. It is only critical that during chlorination the pH thereof be permitted to fall within the reaction range set forth above and be maintained within the range thereafter.

In a second embodiment of the invention, pH is controlled throughout the chlorination of the solution of 2-mercaptopyridine-1-oxide. In this embodiment, an initial pH adjustment is not required unless the starting solution has a pH of less than 4. Generally, however, the solution of 2-mercaptopyridine-1-oxide has a pH in the range of 4 to about 8.5 and may be chlorinated without a pH adjustment. As chlorination commences pH of the reaction mixture drops rapidly and is then controlled in the range of 4–8, advantageously 4–7.6, preferably 5–7.6 during the final stages of chlorination. Chlorination is combined as in the preceeding embodiment until at least 1.0, suitably 1.0 to 2.0, preferably 1.0–1.5 moles of chlorine have been added per mole of 2-mercaptopyridine-1-oxide present.

pH is controlled within the specified range during chlorination by simultaneously or intermittently adding a strong highly dissociated, rapidly reacting base such as sodium hydroxide.

In either embodiment, the chlorination may be carried out at ambient temperature or over a fairly broad temperature range, for example, from about 0° C. up to about 50° C. No reason is seen for operating outside this temperature range although it is possible to do so, if desired. A preferred temperature for the reaction is about 20° C. – 40° C. It is also possible to operate below this temperature range during chlorination and to adjust the temperature to within the range after chlorination to drive the reaction to completion.

The reaction is preferably conducted at atmospheric pressure, but may also be conducted at any other desired pressure, for example, from 0.1–100 atmospheres.

Chlorine is preferably added slowly to the reaction mixture, suitably over a period of 0.25 hours to 5 hours, preferably 0.25–2 hours.

During and after chlorine addition, it is advisable to agitate the reaction mixture in any known manner to avoid localized concentrations of chlorine or base which might adversely affect yields. It is also advisable to agitate for a suitable post-addition time as well. A suitable post reaction time at 20°–40° C. is generally 1 to 5 hours, preferably 2–4 hours for a total reaction time of about 1.5 to 5 hours. In terms of overall productivity, a total reaction time of 2–4 hours is preferred, but reaction times as long as 17 hours have been employed without loss of yields.

In the specific embodiments described above the key to increased yields and improved chlorine utilization appears to lie in the in situ formation of hypochlorous acid as the reactive species. As chlorine is supplied to the reaction mixture at a pH above about 6.8–7.0 in the presence of sodium hydroxide it is taken up in the solution predominantly as hypochlorite anion in accordance with the equation:

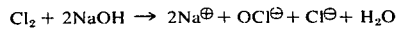

The hypochlorite anion, however, does not appear to oxidize 2-mercaptopyridine-1-oxide to the disulfide. Whether it reacts with it to form some other species or whether the equilibrium in favor of the sodium salt of 2-mercaptopyridine-1-oxide is such as to resist attack by hypochlorite ion is not known.

As pH drops below about 7, however, the equilibrium between hypochlorite anion and hypochlorous acid is shifted in favor of the latter in accordance with the equation:

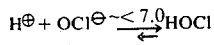

Simultaneously as the pH drops below the neutral point, the equilibrium between the sodium salt of 2-mercaptopyridine-1-oxide and the acid form of 2-mercaptopyridine-1-oxide is also shifted in favor of the latter in accordance with the equation:

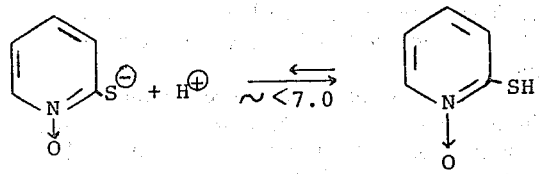

Thus at a pH in the required range, the acid form of 2-mercaptopyridine-1-oxide is oxidized by hypochlorous acid to yield the disulfide in accordance with the equation:

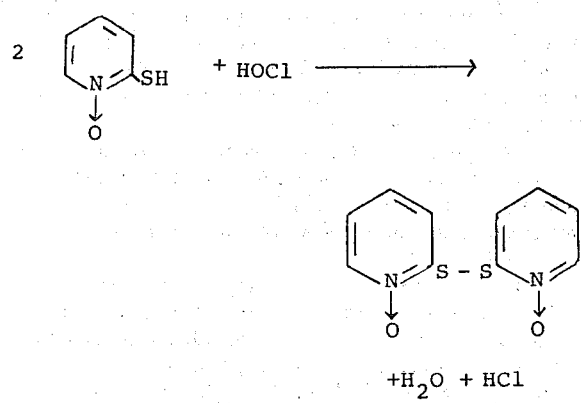

When sodium bicarbonate or a mixture of sodium bicarbonate and sodium hydroxide are present, the oxidation to the disulfide becomes apparent at a slightly higher pH than with sodium hydroxide alone, this enables one to operate at a slightly higher pH with bicarbonate present than with the hydroxide alone. It is believed that bicarbonate causes the oxidation to occur at a slightly higher pH due to the fact that the reaction between chlorine and bicarbonate leads to the direct formation of hypochlorous acid rather than proceeding through the intermediate hypochlorite anion stage.

Thus, if sodium hydroxide alone is employed the range is advantageously 4 up to about 7 preferably up to 6.8 whereas if bicarbonate or a combination of bicarbonate and sodium hydroxide are present, the preferred range is 4 up to about 8, preferably up to 7.6. In either instance the preferred lower pH is about 5.

While 2-chloropyridine is the preferred starting material in the process, other 2-halo-pyridines and substituted halopyridines containing such groups as halogen, lower alkyl and lower alkoxy which do not adversely effect the reaction may also be utilized.

Upon completion of the reaction in accordance with this invention, the disulfide product bis(2-halo-pyridyl-1-oxide) disulfide is isolated by simply filtering the resulting reaction mixture and purifying in a known manner.

The disulfides prepared in accordance herewith have a variety of known uses, particularly as antibacterial and antifungal agents for use in a variety of agricultural and non-agricultural uses and as intermediates for compounds used in toiletry formulations, such as shampoos and for other applications as disclosed in U.S. Pat. No. 2,742,476.

EXAMPLE 1

A 2-liter, 3-neck flask, equipped with thermometer, mechanical stirrer and addition funnel was charged with 1180 g. of a reaction mixture having a pH of 6.4 assaying 8.2% by weight (96.6 g., 0.65 mole) sodium-2-mercaptopyridine-1-oxide, 8% sodium chloride and 14–16% by weight sodium acetate. The pH of this solution was adjusted to 10.2 with concentrated aqueous sodium hydroxide.

A total of 29.5 g. (0.42 mole) chlorine gas was bubbled through the basified solution at 30° C. with rapid stirring over a 30 minute period. The slightly exothermic reaction raised the temperature to 35° C. by the end of chlorination. Rapid stirring was continued 2.5 hours after completing addition of chlorine. The reaction mixture was then filtered to remove precipitated product and the filter cake washed with 50 ml. water, then 50 ml. methanol, finally 50 ml. diethyl ether and air dried. A total of 68 g. (83.2%) of bis(2-pyridyl-1-oxide) disulfide was recovered. The infrared spectrum and melting point (200°–201° C.) were identical to an authentic analytical reference standard of bis(2-pyridyl-1-oxide) disulfide having an assay of 99.4%.

EXAMPLES 2–9

Example 1 was repeated except that initial pH initial and final ph were as shown in Table 1.

Table 1

| pH | | R × N Time | | Temperature | Yield |
|---|---|---|---|---|---|
| Initial | Final | Cl₂ Addn. | Total | (°C.) | (%) |
| 8.0 | 5.1 | 0.5 | 3 | 23–34 | 83.1 |
| 9.1 | 5.3 | 0.5 | 3 | 30–35 | 82.6 |
| 10.0 | 5.0 | 0.5 | 3 | 5–10 | 79.6 |
| 10.1 | 5.4 | 0.5 | 3 | 25–35 | 83.9 |
| 10.3 | 5.1 | 0.5 | 3 | 25–30 | 79.6 |
| 11.9 | 5.5 | 0.5 | 3 | 25–30 | 80.3 |
| 6.4* | 1.2 | 0.5 | 3.5 | 25–30 | 60 |
| ≧7.0 | ≧7.0** | 0.5 | 3.5 | 25–30 | 0 |

*no basification prior to chlorine addition.
**controlled at slightly above 7 with NaOH throughout chlorine addition.

EXAMPLE 10

The reaction mixture of example 1 (622 g. containing 51.0 g., 0.34 mole, sodium 2-mercaptopyridine-1-oxide) and having an initial pH of 6.4 was chlorinated over a period of 0.5 hours with 135 g. (0.19 moles) Cl₂ which was bubbled through the reaction mixture. During chlorination 165 cc 1N NaOH (.165 moles) of sodium hydroxide were added dropwise with stirring to control the pH at 6.0. Temperature of the reaction mixture was 25°–30° C. Following chlorine addition the reaction mixture was stirred for an additional 2.5 hours, and the product recovered as in Example 1. Yield was 80.0%.

EXAMPLE 11

Example 10 was repeated except that 12.8 g. (0.18 moles) of chlorine were utilized and the pH was controlled at 5.6 throughout chlorine addition by dropwise addition of 90 cc 3N NaOH. Yield was 80.5%.

EXAMPLE 12

To 622 g of an 8% solution of 2-mercaptopyridine having a pH of 9.0 was added 14.0 g of $NaHCO_3$, resulting in a pH of 8.0. The mixture was chlorinated over a period of 45 minutes at a temperature of 25°–35° C. with 12.6 g of chlorine. pH of the reaction mixture during chlorination decreased in ten minutes to a pH of about 6.8 and remained at that level, ± 0.15 pH units, until chlorination was complete. The reaction mixture was then stirred for an additional 2.25 hours at which time pH had risen to 7.2. Yield was 82.7%.

EXAMPLE 13

Example 12 was repeated except that 8 gm. of $NaHCO_3$ was added. Again pH dropped during chlorination. At a pH of 6.45 gas evolution ceased indicating that bicarbonate had been used up. Chlorination was continued 13.5 gm. of chlorine had been added at which time the pH of the reaction mixture was 5.7. After stirring for 2.25 hours the pH was 5.6. Product was recovered in a yield of 81.5%.

EXAMPLE 14

To 622 g of the solution of example 12 was added 14 gms. of sodium bicarbonate giving a pH of 8.5 when chlorination was commenced. The mixture was then chlorinated over a period of 45 minutes with about 13 g of chlorine. pH of the reaction mixture declined in the first 10 minutes to about 7.2. Precipitation was noted when the pH passed the 7.6 mark. Upon reaching a pH of 7.2 caustic was added dropwise to control the pH at a value in the range of 7.6–7.8 until the last 5 minutes of chlorination. At that time the reaction mixture was tested with ferric chloride to determine the presence of 2-mercaptopyridine-1-oxide. The test was positive. During the last 5 minutes of chlorination pH was then allowed to decline to a value of 7.2. The ferric chloride test was again performed and found to be negative indicating that the reaction had gone to completion. Product yield was 80.0%.

What is claimed is:

1. In a process for preparing bis-(2-pyridyl-1-oxide) disulfide wherein 2-chloropyridine is oxidized with peracetic acid to form a reaction mixture containing 2-chloropyridine-1-oxide which is mercaptized to form a solution of 2-mercaptopyridine-1-oxide, the improvement which comprises:

Reacting 2-mercaptopyridine-1-oxide with hypochlorous acid, said hypochlorous acid being generated in situ by chlorinating said solution with about 1.0–2.0 moles of gaseous chlorine per mole of 2-mercaptopyridine-1-oxide at a pH controlled within the range of 4–12 with a base selected from the group consisting of alkali metal hydroxide, alkali metal bicarbonate, alkali metal carbonate and mixtures thereof, said base being utilized in an amount sufficient to maintain said pH within said pH range during chlorination and to produce a reaction mixture having a terminal pH in the range of 4–8.

2. The process of claim 1 wherein said base is sodium hydroxide and said terminal pH is in the range of 4 to about 6.8.

3. The process of claim 2 wherein the pH of said solution is adjusted to a pH in the range of 8–12 prior to chlorination, and is permitted to fall during chlorination to a terminal pH in the range of 4 to 6.8.

4. The process of claim 2 wherein the pH of said solution is adjusted to a pH in the range of 10–12 prior to chlorination and is permitted to fall during chlorination to a terminal pH in the range of 4 to 6.8.

5. The process of claim 2 wherein the pH of said solution is adjusted to a pH in the range of 10–12 prior to chlorination and is permitted to fall during chlorination to a terminal pH in the range of 5 to 6.8.

6. The process of claim 2 wherein said pH is continuously controlled to a pH within the range of 4–6.8 during chlorination.

7. The process of claim 1 wherein said base is selected from the group consisting of sodium bicarbonate and a combination of sodium bicarbonate with sodium hydroxide and wherein said terminal pH is in the range of 4 to 8.

8. The process of claim 7 wherein the pH of said solution is adjusted prior to chlorination to a pH in the range of 8–12 and is permitted to fall during chlorination to a terminal pH in the range of 4–7.6.

9. The process of claim 7 wherein the pH of said solution is adjusted prior to chlorination to a pH in the range of 8–12 and is permitted to fall during chlorination to a terminal pH in the range of 5–7.6.

10. The process of claim 7 wherein said pH is continuously controlled to a pH within the range of 4–8 during chlorination.

11. The process of claim 10 wherein said pH is continuously controlled to a pH within the range of 5–7.6 during chlorination.

* * * * *